United States Patent [19]

Scherff

[11] Patent Number: 4,538,794
[45] Date of Patent: Sep. 3, 1985

[54] SAMPLING MOLTEN METAL

[75] Inventor: Helmut Scherff, Neukirchen-Vluyn, Fed. Rep. of Germany

[73] Assignee: Mannesmann AG, Duesseldorf, Fed. Rep. of Germany

[21] Appl. No.: 479,261

[22] Filed: Mar. 28, 1983

[30] Foreign Application Priority Data

Apr. 22, 1982 [DE] Fed. Rep. of Germany ....... 3214898

[51] Int. Cl.³ .............................................. C21B 7/24
[52] U.S. Cl. ..................................... 266/79; 266/226; 73/DIG. 9
[58] Field of Search ..................... 266/79, 86, 226, 88, 266/225; 73/DIG. 9

[56] References Cited

U.S. PATENT DOCUMENTS 2,822,163  2/1958  McFeaters .......................... 266/86
4,239,189 12/1980  Scherff ................................ 266/88
4,258,571  3/1981  Jürgens et al. ................. 73/DIG. 9

FOREIGN PATENT DOCUMENTS 2535060  2/1977  Fed. Rep. of Germany ...... 266/226

Primary Examiner—L. Dewayne Rutledge
Assistant Examiner—S. Kastler
Attorney, Agent, or Firm—Ralf H. Siegemund

[57] ABSTRACT

An apparatus is disclosed for manipulating and handling sampling tubes in relation to a metallurgical vessel. The apparatus includes a generally vertically oriented guide frame, mounted for limited tilting about a horizontal axis. Rails on the guide frame permit a carriage to run thereon, the carriage will carry a measuring lance. A tube manipulator is pivotably mounted to the guide frame, and includes a tube holding structure for holding a tube on an axis leading directly into the vessel and being coaxial with an axis of the lance, as moved by the carriage, while being alternatively positionable in coaxial relationship with a horizontal delivery axis. Tubes are placed into this horizontal delivery axis and such tube is moved toward the manipulator for being gripped by the holder thereon, so that such a tube may be swung into an upright position, as the manipulator assumes a vertical position of coaxial relation of the tube as held with respect to said lance axis, leading directly into the metallurgical vessel.

13 Claims, 9 Drawing Figures

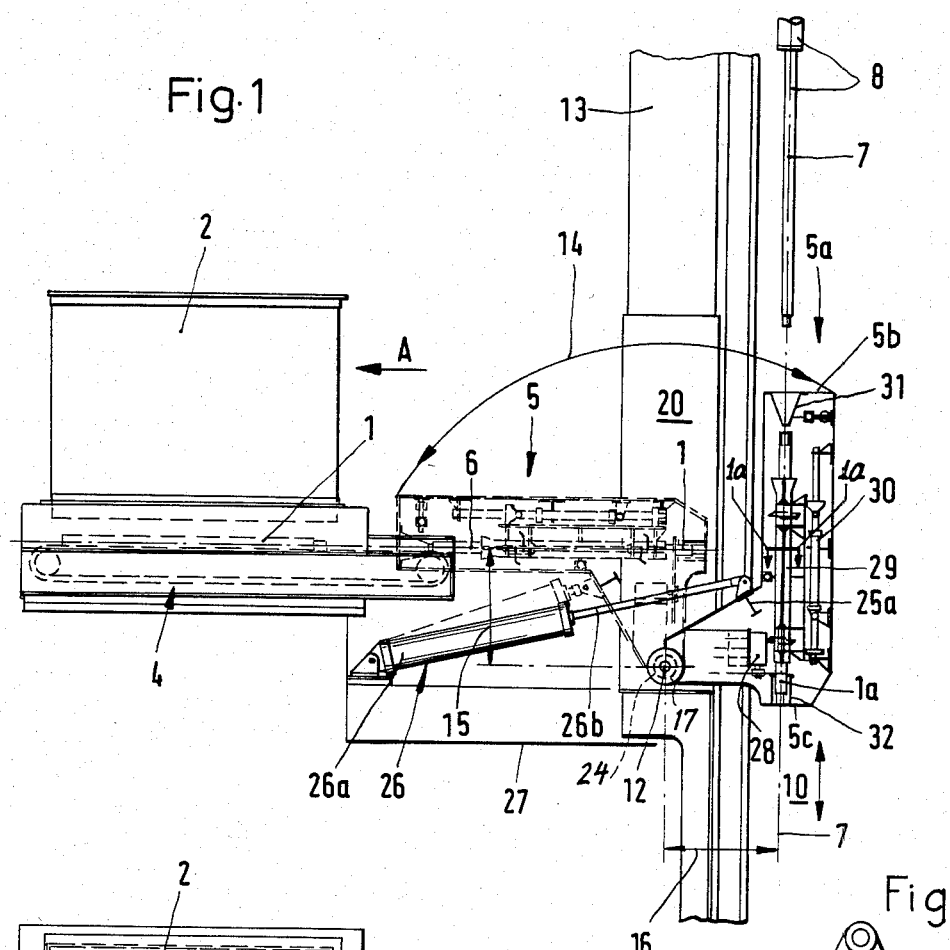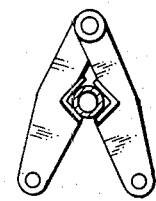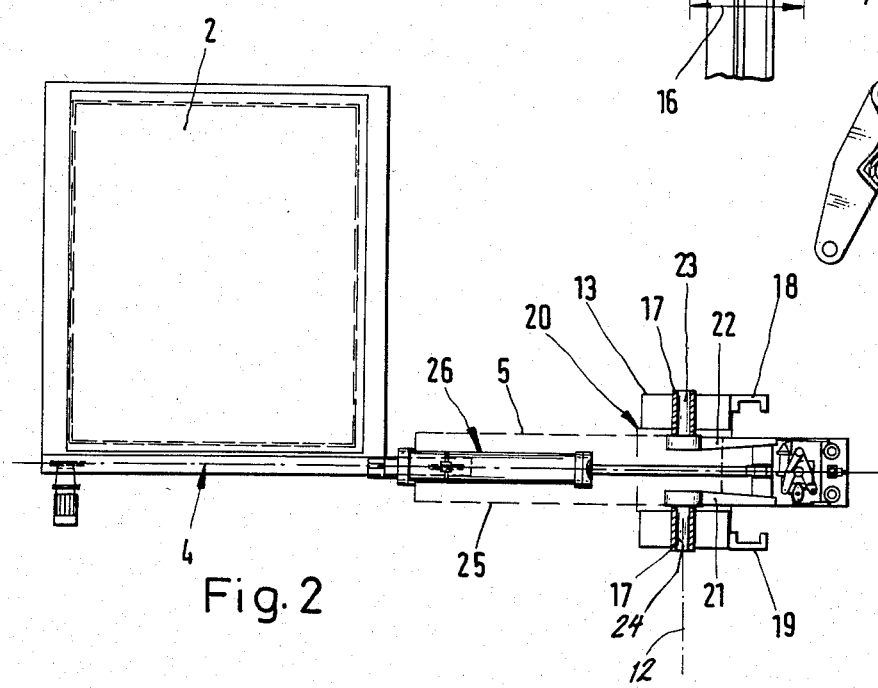

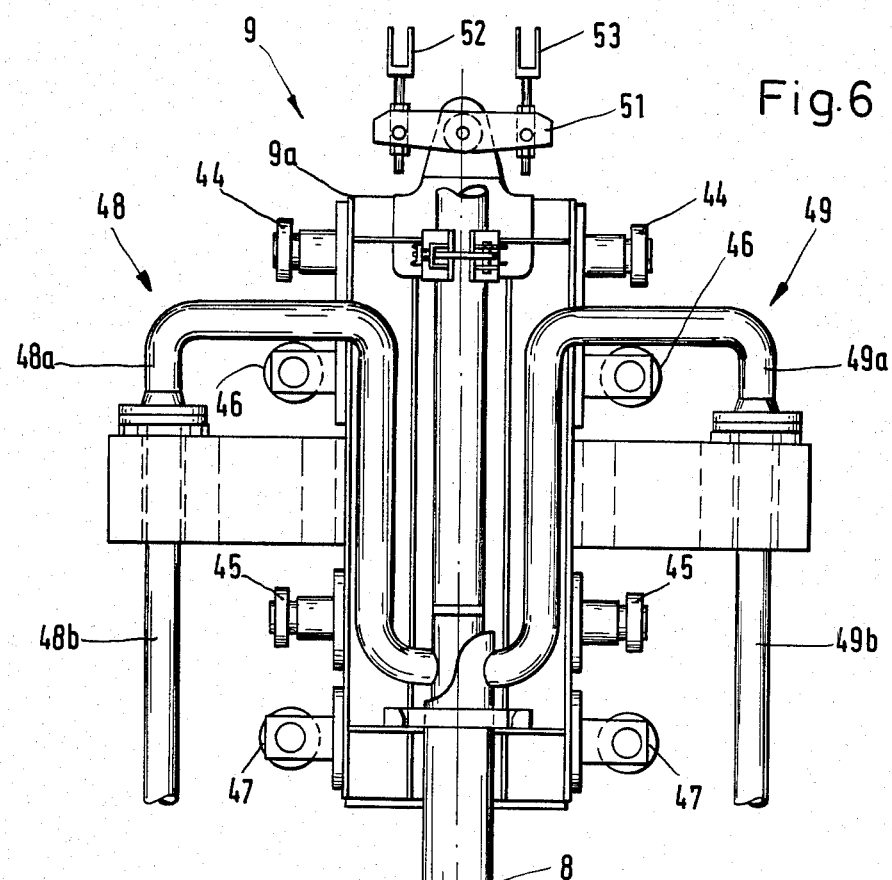
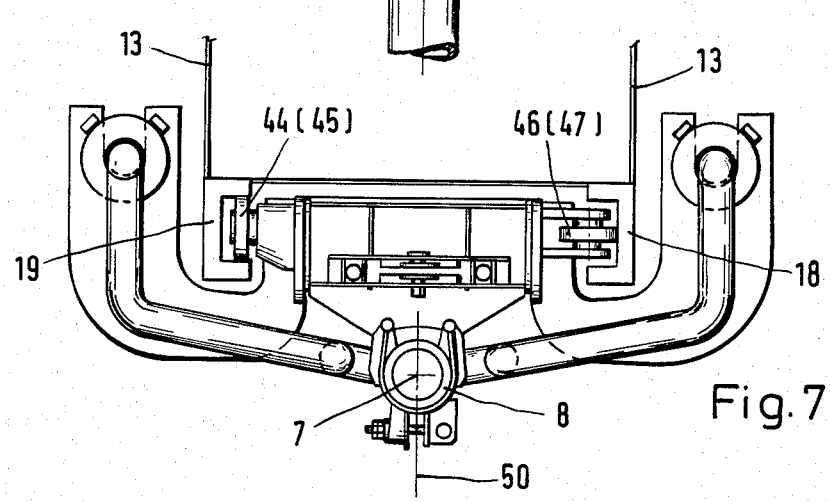

SAMPLING MOLTEN METAL

BACKGROUND OF THE INVENTION

The present invention relates to sampling molten metal particularly steel during its production and more particularly the invention relates to the manipulation of a sampling device including particularly sampling tubes to be taken from a store and to be fastened to a lance for purposes of being lowered into the metal bath and retrieved therefrom.

The manipulation of sampling devices is a task which arises for example, in cases the temperature in the interior of molten metal being subjected to a metallurgical process is to be measured. This is particularly important during steel production. Another mode of sampling involves the removal of a certain amount of metal from the interior of the molten bath and after cooling the sample is to be analyzed for purposes of monitoring the steel making process. In each of these situations, speed and preparedness is of the essence, because the process is a running one and one wants to obtain the respective measuring results as promptly as possible it is inherent in the process that the acquired data are presented and available at a certain delay only and that delay is to be made as short as possible.

The measurements as described are being carried out repeatedly, and one needs therefore a certain number of sampling tubes. These tubes are stored conveniently and have to be removed from the store one by one, fastened to the measuring lance particularly the tip thereof and lowered and raised with respect to the metal bath. Moreover, following such a single cycle, the tube is to be removed, but the sampling device, being for example, a small container has to be removed separately and handled separately for transporting it to the laboratory. From an overall point of view, the several procedural steps and manipulation as described require a certain period of time, and it was found that between 100 and 120 seconds are needed for a complete cycle. On the other hand, a 120 second delay is generally quite long because as stated the process in the interior of the metallurgical vessel continues. Therefore, this cycle time should be made as short as possible, and particularly it should be made shorter than two minutes.

The German printed patent application 2,631,060 suggests the removal of the sampling tube, one by one, from a store and to place it into the operating range of a physically separated handling and manipulating device which receives these sampling tubes and pivots them up into the range of a holding rod being situated in the vicinity of the melting furnace or the like. These individual sampling tubes are now shifted onto the rod. A removal and retrieval device is provided separately therefrom; it operates independently from the afore mentioned tube manipulation device. The advance and retrival device is another piece of handling equipment being pivotably disposed in the range of the furnace opening so that the holding devices will be placed into the vicinity of this opening only when a sample is to be taken and removed from the furnace.

It can readily be seen that the entire known procedure of tube handling requires several transporting steps such as a step by means of which the tube is taken from the store and handled by the manipulator; another step transfers the tube from the manipulator to the pivoting device; another step requires affixing thee tubes to the measuring lance and after insertion and removal of the lance the tube has to be returned to the pivoting device. All these steps are carried out sequentially and each of them requires inherently a certain amount of time. Thus, the cycle time being the sum total of all these delays is long accordingly. As stated, manipulating a plurality of sampling tubes requires inherently a certain period of time so that a finite cycle time is inevitable. But the number of manipulating steps should be made as small as possible so that inherently a reduction of the time for some or all of these steps amounts to a shorter overall cycle time. Independently therefrom it was found that the known equipment handling the tubes require not insignificant amounts of space while on the other hand the space in and around metal processing equipment such as steel making furnace is limited.

DESCRIPTION OF THE INVENTION

It is an object of the present invention to reduce the number of functional and manipulatory steps for handling sampling tubes so as to reduce overall measuring cycle time in the process of sampling in the general sense and involving a molten steel bath or other metal bath so that for example, on one hand, the number of measurements and sample steps per unit time can be increased and the delay between the sampling proper and the acquisition of the gathered data in each sample run is reduced.

It is another object of the present invention to provide a structure for sample tube manipulation in the vicinity of a metallurgical installation which is of compact design, reduces any transport path length and particularly takes the limited amount of available space into consideration.

It is another object of the present invention to provide a new and improved apparatus for handling sampling tubes in relation to a metallurgical vessel as well as in relation to a measuring lance being movable on a vertical measuring axis in relation to such vessel, for temporaryly placing a sampling tube into the vessel and retrieving it therefrom.

More generally it is a particular object of the present invention to provide a new and improved apparatus for handling sampling tubes in relation to a metallurgical vessel and in conjunction with a measuring lance movable on a vertical measuring axis in relation to such vessel.

In accordance with the preferred embodiment of the present invention, the objects of the invention are realized by the utilization of a manipulator which is mounted for pivoting on a horizontal axis and carries releasable means for holding a sampling tube in an upright position such that a tube as held assumes a coaxial position with respect to the measuring axis along which the measuring lance is going to move towards the metallurgical vessel. The releasing means release the tube they hold when in this vertical position and after connecting the tube to the lance; on the other hand, such a tube is initially in a coaxial position with respect to a transport and delivery axis when the manipulator is in a horizontal position there being stationary means including, for example, a store for moving fresh tubes into the transport axis and there along until being held by the releasable means on the manipulator when in the horizontal position. The manipulator is pivoted to a generally vertically oriented guide frame on which runs a carriage which carries the measuring lance for movement along the measuring axis. The guide frame itself is preferably mounted for limited pivoting about a horizontal axis. The frame moreover is provided with a window through which the manipulator can pass when swung into an upright position. Also the rail on the guide frame are provided as tracks for the carriage and are spaced apart so that the manipulator can pass through for the safely; there being a window like construction accordingly.

It can thus be seen that in accordance with the present invention the manipulator has initially a horizontal position with releasable clamping means being disposed in relation to a delivery axis, and a tube such as a sampling tube is moved on that axis until having a particular desirable position in relation to the manipulator in which the releasable means will close to hold that tube. By means of a simple pivoting and swing-up motion by about 90° that tube is placed upright and into the measuring axis and will now be connected to the measuring lance. After the clamping means on the manipulator releases the tube, the manipulator is swung back into a horizontal position while the measuring lance with mounted on tube are moved down by the carriage so that the measuring and sampling tube is placed (at least in parts) into the metallurgical vessel tube to be immediately retrieved therefrom by retraction of the carriage whereupon the measurement or sample taken can be handled in any desirable manner.

It was found that this particular mode of operation of the particular construction permits a considerable reduction in cycle time. As soon as the sampling tube is gripped by the manipulator it merely needs to be swung up by about 90° whereupon the tube is connected to the lance and released from the manipulator; this is the beginning of the measuring cycle proper. In the meantime the swing down motion of the manipulator permits already preparation of the next measuring and sampling tube. In addition, and as soon as the manipluator swings down a centering device is placed in position by means of which coaxial advancement of the lance and of the tube to be interconnected can be assured.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a vertical section view through a sampling tube handling device constructed in accordance with the preferred embodiment of the present invention for practicing the best mode thereof. The drawing shows particularly a tube store and manipulator and a guide frame;

FIG. 2 is a top view of the device shown in FIG. 1;

FIG. 6 is a front view of a measuring lance carrying slide;

FIG. 7 is a top view of the device shown in FIG. 6; and

Proceeding now to the detailed description of the drawings. The measuring or sampling tubes are usually made of cardboard or the like and a plurality of such tube 1 is shown in the several figures. A fairly large plurality is particularly shown in FIG. 3. These tubes are presumed to have in their interior and ends the requisite elements for purposes of interest in the particular process. For example, these tubes may include temperature measuring devices in their interior or at one end or structure may be provided which permits the sampling of gas or other structure which permits sampling the steel itself and removal thereof from the interior of a metallurgical vessel which contains molten metal such as steel; see vessel 11 in FIG. 8.

Figure 3:
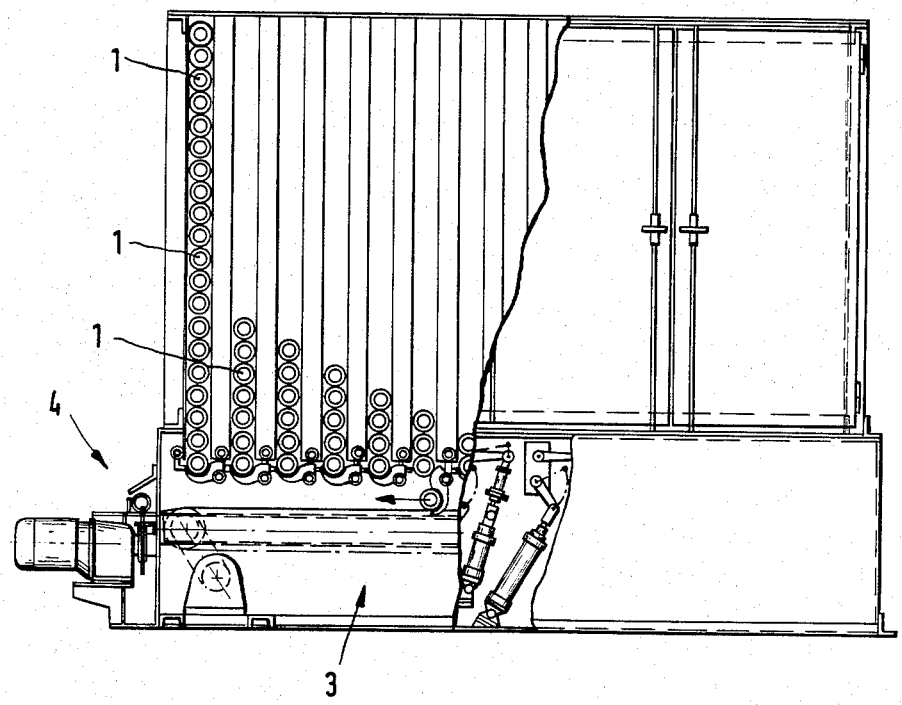
FIG. 3 is a front view of a part of the device shown in FIG. 1 as indicated by the arrow A in FIG. 1.

The tubes 1 are presumed to be stored in a storage facility 2 and in an arrangement shown in FIG. 3 wherein the tubes extend transversely to the plane of the drawing. FIG. 1 shows the tubes in a position parallel to the plane of the drawing. These tubes are vertically staked in a horizontal disposition in the store and in that position they are being taken by means of a transverse manipulator. The vertcal stack channels are closed at the bottom by pneumatically or hydraulically operated contour flaps which can place one tube at a time onto an endless belt 3a for moving the tube transversely to its own axis towards a transport device 4. Device 4 includes also an endless beet and moves the tube towards a manipulator 5. The transport device 4 as well as the manipulator 5 are constructed and positioned so that any particular sampling tube they hold respectively are located concentric to a transport and delivery axis 6.

After the manipulator 5 has assumed the vertical or upright manipulator position 5a the respective sampling tube 1 will be positioned in a particular axis 7 and the equipment is designed and positioned so that axis 7 coincides exactly the measuring axis along which the tube 1 will be moved towards the metallurgical vessel. During this operation, a measuring lance 8 holds that tube and is moved on the axis 7 particularly by means of the slide or carriage 9 as shown in FIGS. 6 and 7. Measuring lance 8 and carriage 9 move on and along the measuring track 10 (FIG. 8) which is defined by the profile of the measuring lance and by the carriage 9. In other words, the carriage tracks are arranged such that the lance 8 on the carriage 9 moves on exactly that axis 7 into which manipulator 5 places the tube 1 when in the upright position.

Figure 8:
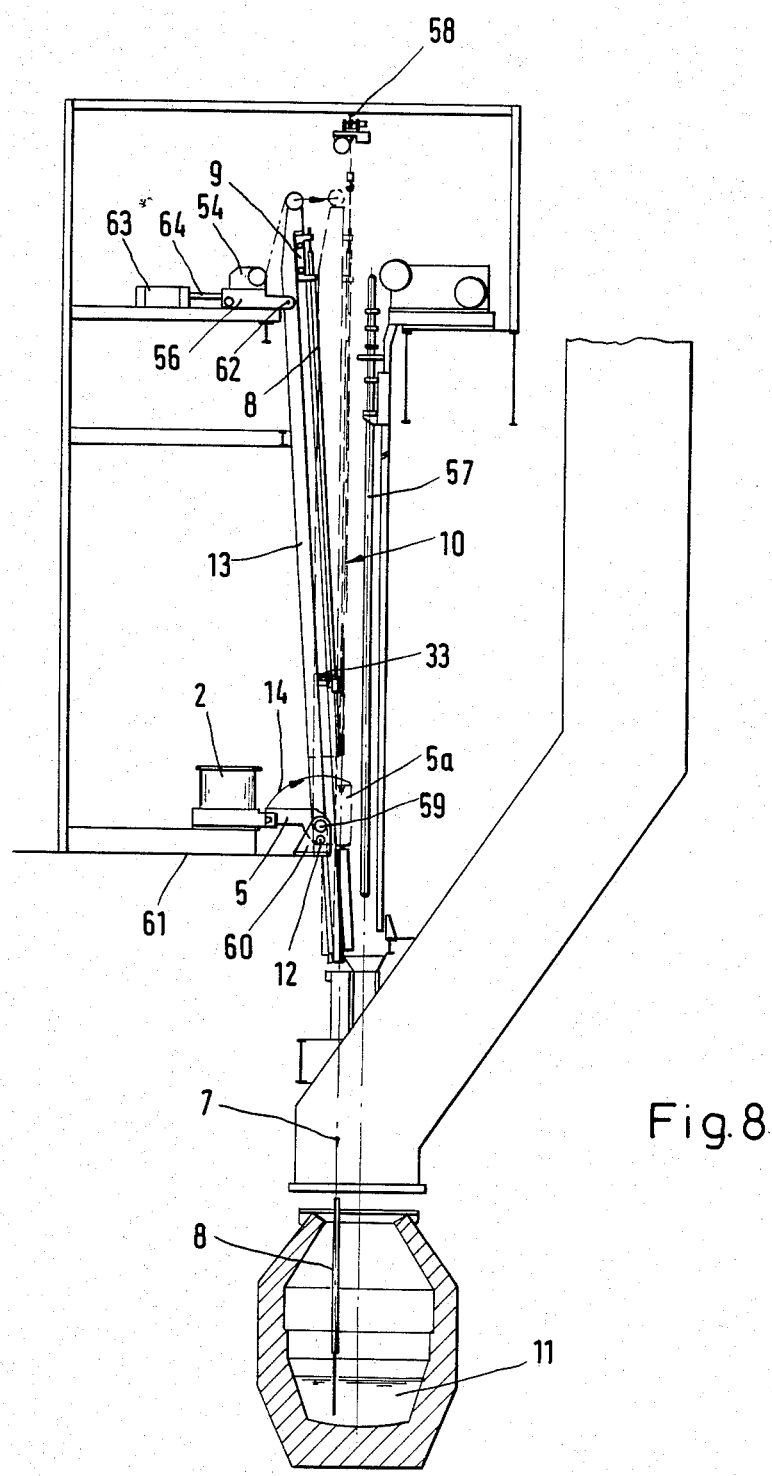
FIG. 8 is the front view of a complete handling system in a steel making facility with tiltable guide frame.

As shown in greater detail in FIG. 8, the measuring lance 8 carries on its tip a sampling tube 1 and is moved by means of the carriage 9 in accordance with the particular sampling procedure towards the metal bath 11. The tube dips briefly into the bath and is retracted immediately thereafter. Subsequently, one will for example separate a portion from the sampling tube for example the portion carrying a metal sample and transport it in a suitable manner to a laboratory or the like. The remainder of the tube is just removed and disposed of.

As can be seen by comparing FIGS. 1 and 8, the manipulator 5 can be pivoted about a pivot axis 12 which extends transversely to the plane of the drawing of FIG. 1 and pertains to a shaft journaled in a guide frame 13. Double arrow 14 delineates a circular art describing geometrically the pivot and tilting motion of manipulator 5 by means of which the tube in the manipulator is moved from a position coaxial with the delivery axis 6 to a vertical and upright position coaxial with the axis 7.

In view of the circular contour of arch 14, the distances 15 and 16 respectively between axis 12 and the transport and delivery axis 6 on one hand, and the axis 12 and measuring axis 7 on the other hand, are equal. This operational and design feature is not essential in principal, because the handling motion of the tube 1 could be a combined rotatory and translatory motion, in which case, distances 15 and 16 may differ by a component equal to or being representative of the translatory displacement component. However a simple tilting motion is preferred.

Tilting bearings 17 for the manipulator are rigidly secured to the guide frame 13 as illustrated in FIG. 2. Moreover, the manipulator 5 moves between rails 18 and 19 for the carriage 9 and through an opening or window 20 in the guide frame 13. The skeleton like frame of the manipulator 5 is comprised of side pieces 21 and 22 respectively secured to pivot pins 23 and 24 which are received by and in the pivot bearings 17.

All these elements as well as other elements to be described below and pertaining to the manipulator 5 are housed in an enclosure 25 which is provided for protective purposes and encloses these parts to protect them against the exterior as much as possible. Of course, a complete enclosure is feasible, but the particular enclosure part provides ample protection against undue soiling.

A pivot drive 26 is disposed underneath enclosure 25. The pivot drive may be a hydraulic or a pneumatic piston cylinder drive unit having a cylinder 26a being linked to a consol 27 of the guide frame 13. The drive has also a piston rod 26b which is articulated to a transverse strut 25a of the enclosure 25. A cutting device 28 is pivoted inside manipulator 5, the cutting device being provided for separating, for example, the front end of a measuring and sampling tube from the remainder thereof. This cutter is comprised of a motor with a circular saw. Moreover, brackets 29 which can open and closed for clamping are movable in the direction parallel to the measuring axis 7 by means of an axial adjusting and actuating mechanism 30. These brackets permit moving the sampling tube towards the measuring lance 8, and they can also be used for separating the lance 8 from the tube after the sampling process and particularly for cutting the portion 1a from the remainder of this tube by means of the cutting device 28. The cut off front portion of the tube will then be moved, for example, by means of a conveyor belt (not shown) to a laboratory.

A guide funnel 31 is provided in the upper portion 5b of the manipulator 5 and here particularly in the interior thereof for guiding the lance 8 and a tube 1 towards each other in a registering relationship. A sleeve 32 is provided in the lower part 5c of the manipulator 5 and serves as a thrust block for ensuring a proper position for cutting the tube 1 in the range of the cutting device 28. Both elements 31 and 32 are positioned coaxially on the axis 7.

Figure 4:
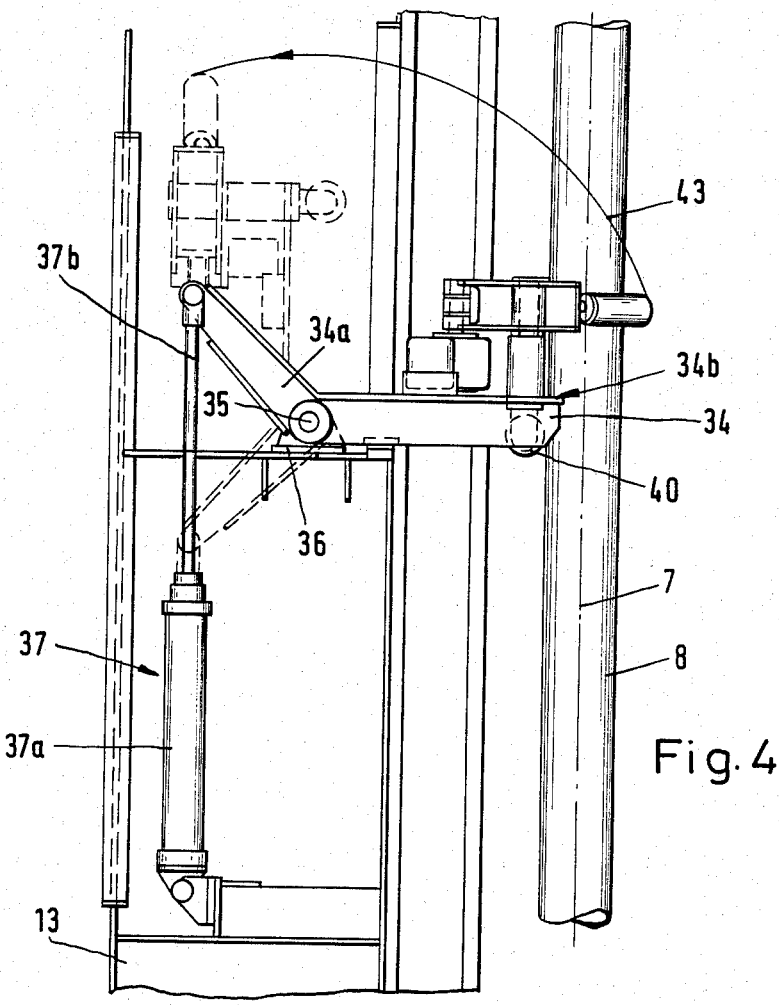
FIG. 4 is a vertical cross sectional view through the guide frame with centering device that is included in the arrangements shown in FIGS. 1, 2 and 3 the drawing being on an enlarged scale.
Figure 5:
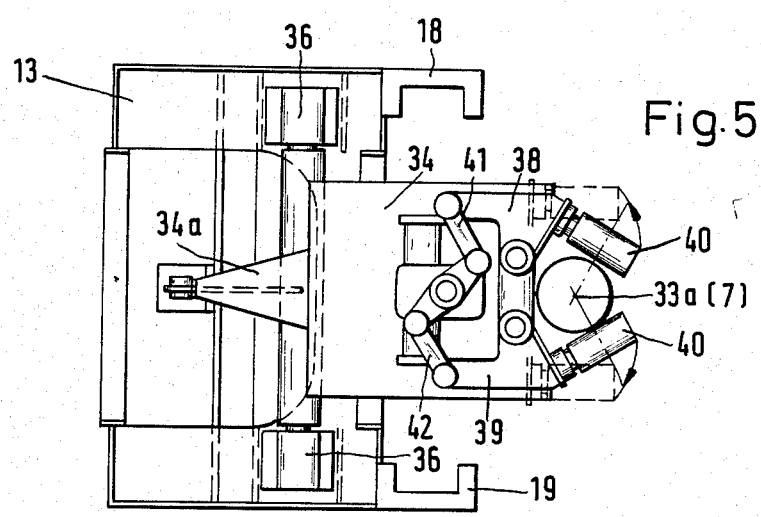
FIG. 5 is a top view of the structure shown in FIG. 4.

It has to be observed that in practice the lance 8 will not remain consistently straight. For this reason a centering device 33 is provided as shown in FIGS. 4 and 5 which is preferably arranged to be situated in the end portion of lance 8. Device 33 is provided to avoid any deviation of the measuring axis 7 with respect to the elements of manipulator 5. The centering axis 33a coincides with the measuring axis 7 in this particular example.

The centering device 33 should be ameanable to pivoting or tilting out of the measuring track 10. Accordingly a rocking arm 34 is provided and journaled in pivot bearings 36 for pivoting and turning about the horizontal axis 35. The pivot bearings 36 are secured to the guide frame 13. Moreover, a pivot drive 37 is provided at the guide frame 13 and being constructed as a hydraulic or pneumatic operating, piston-cylinder drive and arrangement. A piston 37a of that drive is articulated to the guide frame 13, and the piston rod 37 is articulated to a lever arm 34a of the pivot or rocking arm 34. Rocking device 34 is additionally provided with a plate 34b supporting levers 38 and 39 for pivoting about vertical axes (pivots 38a and 39a). One end each of these levers carries centering elements 40a, b, c and the other ends are respectively connected with adjustment, actuator and drive elements 41 and 42. The connection of levers 38, 39 to elements 41, 41 respectively are made so that upon actuation two of the centering elements 40a, b, c function equivalent to plyers with similar closing paths, elements 41 and 42.

One of the centering elements 40a is situated in a lower plane but cooperates with the two others 40b, c. The centering elements together are constructed as rolls and serve also as stops; they are distributed at a 120° angular spacing for actioning as limiters of the displacement of the measuring lance 8. The rocking arm 34 will be pivoted to assume the dashed position upon retraction of the piston rod 37b whereby the centering elements 40a, b, c undergo pivot motion along the circular arc 43.

The carriage 9 (FIGS. 6 and 7) is constructed to have a frame 9a to which are connected pairs of wheels 44 and 45. The wheels of these pairs run on the inside of profiled rails 18 and 19. The wheel pairs 44 and 45 thus position positively the carriage 9 in the relation to a first plane. Additional wheel pairs 46 and 47 position the carriage 9 in relation to a second plane which intersects the first one at right angles. The measuring lance 8 is situated centrally on the carriage 9 and runs in and along the measuring axis 7. This particular operating condition must not be interfered with by the weight of cooling feed ducts 48 and 49. These ducts 48 and 49 are composed of nonflexible sections 48a and 49a respectively on one hand and flexible sections 48b and 49b on the other hand. They are situated strictly symetrical to the vertical plane 50 in order to obtain balanced conditions which will not cause the carriage to deviate from the prescribed path and disposition vis-a-vis the above mentioned planes. In addition, the flexible sections 48b and 49b extend outside the periphery of the guide frame 13 and are therefore favorably constructioned with regard to the basis concept namely to position the manipulator 5 for placing tubes along the shortest possible path directly into the desired operating position vis-a-vis the measuring axis 7. The measuring lance carriage 9 is suspended from a rope drive 54 by means of a scale bar 51 and tension members 52 and 53. The drive 54 itself is arranged on a carriage 56.

The space available in a steel production and processing facility is quite limited; particularly and for example, for reasons of the requisite oxygen lance 57 which is needed for blowing in steel production. The measuring lance could be operated parallelly to the oxygen lance 57; however in a large number of cases there is not enough space for moving a new blowing lance to the equipment and removing the old one therefrom and to do the same with regard to the measuring lance. It has to be considered that in both instances reserve equipment is needed and has to be moved into place.

Another aspect is the following: the particular metallurgical vessel is usually arranged in relation to and under a single crane track 58 being in fact arranged to run across a narrow pit. The direction of movement of the crane of course extends transversely to the plane of the drawing of FIG. 8. Accordingly, the guide frame 13 for the measuring lance 8 is tiltably mounted for tilting about a horizontal axis 59 which is situated in the vicinity of the pivot axis 12 for the manipulator 5. This way the requisite space for any exchange of lances is provided for. Reference numeral 60 refers to the pivot bearings which are mounted to a stationary frame part 61. The guide frame 13 is connected to the carriage 56 by means of a pivot joint 62. Moreover, the carriage 56 is connected to a stationary push drive 63 via pushing rod 64. The push drive 63 and the carriage 56 together constitute the tilt drive for the guide frame 13 tilting motion being directly imparted upon the frame 13 via the push rod 64.

It can thus be seen that the equipment constructed in accordance with the invention for purposes of achieving the desired objective and for carrying out the inventive method is based on a turnable or tiltable manipulator with a horizontal tilting axis and cooperating with a store for sample tubes in such a manner that the manipulator 5 is in fact placed just opposite the guide frame 13 for the carriage 9 operating in the vertical. Upon choosing the distance 16 between the measuring axis to the horizontal pivot axis 12 and the distance 15 between the horizontal pivot axis 12 of the manipulators to the horizontal transport axis 6 for the tubes equal, one establishes a simple circular displacement path (14) for the manipulator 5 without supplemental translation displacement.

The construction as shown in of a very compact nature not only because the store 2 is positioned right next to the manipulator 5 but no additional pivot structure is needed. The particular tilting of the manipulator moreover permits rapid clearing of the measuring path for passage of the measuring lance 8 to which the new tube 1 has just been affixed. On the other hand, the inventive guide frame 13 relieves other equipment which are usually required for blow lance technique in the case of oxygen blowing for steel making. In particular, the guide frame 13 permits the separation of the entire tube manipulation structure from the portion of the metallurgical arrangement such as the oxygen feeder arrangement under consideration of the lack of available space.

The inventive guide frame 13 moreover is particularly effective by the specific feature according to which the manipulator 5 being tiltable about horizontal axis 12 can pass between the rails 18 and 19 of the carriage 9 while being temporarily placed into the vertical position. This constructive feature is based on the discovery that upon considering the diameter of the tubes 1 one needs only a rather narrowly constructed manipulator as such, and that in turn permits its passage between the rails 18 and 19. In view of the fairly large dimensions for the guide frame 13, it is advisible to incorporate in the construction a window or opening such as 20 in the guide frame for passage of the tiltable manipulator. In view of the static mechanics of the guide frame such a window is particularly suitable and can take up considerable load. This basic construction feature is highly instrumental in juta supposing generally the manipulator as such in relation to the measuring track which is defined by these rails 18 and 19.

As stated, the manipulator 5 is generally placed in an enclosure 25 and the tilt drive for the manipulator is placed within that enclosure and underneath the manipulator proper. This protective feature is beneficial for the protection of the hydraulic or numatic drive and from an overall point of view it contributes to the compactness of the construction as a whole because, as stated, saving space is of the essence.

The elements manipulating the tubes should be protectively disposed inside the manipulator itself. This way one obtains additional advantages. For example, the brackets 29 for holding the tubes more or less centrally are constructed with an angular cross section and they are arranged in the manipulator symetric to the measuring and transport axes. This central disposition makes possible the placement of other elements near the end portions of the tube as held in the manipulator and the central holding of the tubes is particularly safe for maintaining a particular desired position of the respective vis-a-vis the manipulator, because the manipulator in turn is accurately positioned with regard to the transport axis and the measuring axis.

The compact construction as outlined above, carries with it further advantages. The clamping brackets 29 are associated with the guide funnel 31 and the guide sleeve 32 which are arranged in coaxial relationship to each other from an overall point of view. This arrangement is a serial one, involving the funnel, the brackets and the sleeve and facilitates greatly the affixing of the tubes to the measuring lance while clearing the manipulator after use and removal of the tube. The latter manipulation is likewise facilitated by that arrangement for running the measuring lance 8 into the guide and centering funnel 31. Their alignment can be a problem particularly if after a long use the measuring lance is no longer truely straight and of course, lance 8 and sample tube 1 have to be precisely coaxial to each other in order to permit a rapid afixation of one to the other.

The fastening operation of lance and tube are facilitated by the centering structure 33 which of course has to be situated also in the measuring path (axis 7), but must be removable to clear that path. It is for this reason that the centering device 33 is constructed for pivoting in a vertical plane such that the centering axis coincides with the measuring axis 7 when the components considered are in position. This is the reason for constructing the centering device 33 as a rocking arm 34 for pivoting about a horizontal axis by means of the tilt drive 37 causing the arm 34 to be tilted in the vertical (FIG. 4). This way one removes the centering device 33 very effectively from the measuring path; the off position is to be maintained only for a short period and during the measuring cycle porion proper.

The basis concept of the construction in accordance with the invention is also of advantage for auxiliary equipment relevant for measuring and sampling. The measuring lance carriage 9 of course provided with all the requisite connections to and from the measuring lance and the tube. This means that a certain load is exerted upon the carriage which may tend to tilt the carriage out of its vertical tract and guide path. Such displacement of the carriage could lead to significant interference particularly during rapid lowering of the carriage. Also, unequal load on the guide mechanism as a whole may lead to rapid wear of engaging parts particularly on the carriage and of the track parts. Unequal moments may particularly occur if coolant is not fed to the system symetrically because weight of the the coolant constitutes a heavy load mechanically. A symetrical arrangement of feeding and discharging the coolant, particularly with regard to a vertical plane of symmetry that includes the measuring axis on one hand is very important for obtaining mechanically balanced conditions. Upon placement of the coolant feed and discharge paths and conduits outside the guide frame 13 one equalizes and balances the load on the carriage. This arrangement, moreover, is beneficial particularly with regard to the condition that the manipulator is movable within the boundaries of the guide frame 13 and is also movable between the tracks for the carriage as was outlined above.

A complete cycle of operation includes the following manipulatory steps and is carried out by the following sequence of operations. At a certain point in time one of the gates or bottoms of the store 2 are opened by their respective hydraulic or pneumatic drives to deposit a tube 1 onto an endless belt 3a for moving such a tube towards the longitudinal conveyor 4. The conveyor moves the particular tube 1 along the axis 6 towards the manipulator 5 assumed to be in a horizontal disposition. As the tube 1 enters the manipulator 5, it is gripped by the structure and clamping brackets 29. At a time when measuring is desired, the tilt drive 26 tilts the manipulator 5 so that the tube 1 held therein is placed into an upright position, particularly a position in which the axis of the tube is coaxial with the measuring axis 7. The carriage 9 has been retracted previously so that the lance 8 is retracted accordingly. Also prior to the placement of the manipulator 5 into the upright position the centering device 33 has been retracted by operation of the drive 37.

As soon as the tube 1 held by the manipulator is placed in axis 7 lance 8 is advanced by the carriage 9 and the end of lance 8 is affixed to the tube 1. This connection requires that the lance 8 and the tube 1 are precisely aligned in a registering position and here the sleeve 32 is instrumental for particularly positioning the tube 1 while on the other hand the funnel 31 guides the lowering of the measuring lance 8 towards a registering position with the tube 1. Next the tube 1 is going to be affixed to the lance 8, the brackets 29 open, and the manipulator 5 will return by tilting it back into the horizontal position for receiving another one of the tubes from store 2. In the meantime (and this is important because these operations can concur) centering device 33 is pivoted about a horizontal axis by means of the drive 37 to be placed into the range of the lance 8 for gripping the same, or, more precisely, for causing the rolls 40a, b and c to engage the lance 8 in a stabilizing, three point engagement. Now the operation can begin which constitutes the basic purpose of entire arrangement, namely placing the lance into a position so that the sampling tube 1 and particularly the front portion thereof can perform the desired sampling function which requires the lance to be lowered so that the tube 1 can fit into the vessel 11 as shown in FIG. 8. Following the sampling operation the carriage 9 retracts the lance and the tube 1 whereupon the cutting device 28 cuts, for example, the lower front end of the tube 1 to be captured suitably in arrangement now shown and to be transported to a laboratory. Also, the tube 1 is to be removed from the lance 8 in a suitable arrangement whereupon the lance 8 is retracted from the measuring zone by upward movement of carriage 9. In the meantime the manipulator 5 has received another tube 1 and whenever it is appropriate, the tube 1 will be tilted into an upright position for affixing to the lance 8 so that another measuring cycle can begin.

The invention is not limited to the embodiments described above, but all changes and modifications thereof not constituting departures from the spirit and scope of the invention are intended to be included.

I claim:

1. Apparatus for handling sampling tubes in relation to a metallurgical vessel and measuring lance movable in a vertical measuring axis in relation to said vessel for temporarily placing a sampling tube into the vessel and retrieving it therefrom, comprising:
   a manipulator mounted for pivoting on a horizontal axis;
   releasable means on the manipulator for holding a sampling tube such that the tube is coaxial with that measuring axis when that manipulator is in an upright pivot position, and directly above the metallurgical vessel, said releasable means releasing the tube when in the vertical position for connection of the tube to the lance, the tube being coaxial with a delivery axis when the manipulator is pivoted into a horizontal axis; and
   stationary means for moving a fresh tube in and along said delivery axis for being held by said releasable means.

2. Apparatus as in claim 1 and including a centering device for the lance, being pivotable on an axis for selective placement in relation to said lance independently from the manipulator, the centering device being removed by pivoting when the manipulator is in the upright position.

3. Apparatus as in claim 2 and including a guide funnel coaxially mounted to said manipulator and further including a guide sleeve coaxially mounted thereto, said releasable means on the manipulator being disposed in between the guide funnel and the sleeve.

4. Apparatus as in claim 1 said releasable means including clamping brackets of rail like configuration with angular cross section.

5. Apparatus for manipulating sampling tubes in relation to a metallurgical vessel comprising:
   a generally vertically oriented guide frame, there being spaced apart guide rails on the frame, said guide frame being pivotably mounted for limited pivoting on a horizontal axis; drive means connected to and acting upon said guide frame to obtain a pivoting thereof.
   a carriage running on the frame in a vertical direction towards and away from the vessel along a measuring axis for obtaining the taking of samples.
   a measuring lance on the carriage; a pivotable centering device for the lance for placement of the lance into said measuring axis and for removal therefrom.
   a tube manipulator pivotably mounted to the frame; and
   tube placing means on the manipulator for holding a tube in a position coaxial with said lance when the manipulator is in an upright position and placing the tube coaxially with a delivery axis when the manipulator is in a horizontal position, the manipulator passing in between the rails upon pivoting into the vertical position.

6. Apparatus as in claim 5 said frame having a window for passage of said manipulator.

7. Apparatus as in claim 5 and there being enclosure means for partially enclosing and protecting the manipulator.

8. Apparatus as in claim 5 and including hydraulic or pneumatic drive means connected to the manipulator for causing a pivoting thereof.

9. Apparatus as in claim 5 the centering device including a rocking device carrying at least two centering elements the rocking device being tiltable about a horizontal axis; and drive means connected to and acting upon said rocking device to obtain pivoting thereof.

10. Apparatus as in claim 5 and including cooling means for said lance, the cooling means being disposed symmetrical to and generally outside said guide frame, said manipulator being positioned in between said cooling means upon having a vertical tilted position.

11. Apparatus for manipulating and handling sampling tubes in relation to a metallurgical vessel comprising:

a generally vertically oriented guide frame mounted for limited tilting about a horizontal axis, there being rail means on the guide frame;

a carriage running to the frame in said rail means and carrying a measuring lance;

a lance centering device tiltably mounted on the frame and having retractable centering means for engaging the lance;

a tube manipulator pivotably mounted to the guide frame and including tube holding means for holding a tube on an axis leading directly into the vessel and being coaxial with an axis of said lance as moved by the carriage and alternatively in coaxial relationship with a horizontal delivery axis; and means for placing tube into said horizontal delivery axis and moving a tube towards the manipulator for being gripped by the holding means so that such a tube may be swung into an upright position as the manipulator assumes a vertical position of coaxial relationship of the tube as held with respect to said lance axis.

12. Apparatus as in claim 11 said manipulator including centering means for cooperation with said lance to permit said tube to be inserted and affixed to said lance in coaxial relationship therewith as the lance is moved by said carriage towards said tube when held by said manipulator in the upright position.

13. Apparatus as in claim 12 and including balanced coolant feeding and discharge means being symmetrically disposed with respect to said lance.

* * * * *